United States Patent
Yazdanfar et al.

(10) Patent No.: US 9,273,950 B2
(45) Date of Patent: *Mar. 1, 2016

(54) SYSTEM AND METHOD FOR AUTO-RANGING IN OPTICAL COHERENCE TOMOGRAPHY

(75) Inventors: Siavash Yazdanfar, Niskayuna, NY (US); Sora Kim, Niskayuna, NY (US); Chulmin Joo, Kyunggi-do (KR)

(73) Assignee: General Electric Company, Schenectady, NY (US)

( * ) Notice: Subject to any disclaimer, the term of this patent is extended or adjusted under 35 U.S.C. 154(b) by 1049 days.

This patent is subject to a terminal disclaimer.

(21) Appl. No.: 13/335,211

(22) Filed: Dec. 22, 2011

(65) Prior Publication Data

US 2013/0162948 A1    Jun. 27, 2013

(51) Int. Cl.
A61B 3/14     (2006.01)
G01B 9/02     (2006.01)
A61B 3/10     (2006.01)
A61B 3/12     (2006.01)

(52) U.S. Cl.
CPC ............ G01B 9/02044 (2013.01); A61B 3/102 (2013.01); A61B 3/12 (2013.01); G01B 9/02048 (2013.01); G01B 9/02063 (2013.01); G01B 9/02064 (2013.01); G01B 9/02091 (2013.01)

(58) Field of Classification Search
CPC ...... A61B 3/152; A61B 3/145; A61B 3/1015; A61B 3/14; A61B 3/12
USPC .................................. 351/205, 206, 208, 246
See application file for complete search history.

(56) References Cited

U.S. PATENT DOCUMENTS 7,824,035 B2 * 11/2010 Yamada et al. ............... 351/206
2008/0266440 A1 10/2008 Yazdanfar et al.
2010/0165291 A1 * 7/2010 Sugita et al. .................. 351/206

OTHER PUBLICATIONS

Siavash Yazdanfar, et al.; Simple and Robust Image-Based Autofocusing for Digital Microscopy; Jun. 9, 2008, vol. 16, No. 12/Optics Express 8670.

* cited by examiner

Primary Examiner — James Greece
(74) Attorney, Agent, or Firm — Jean K. Testa; Fletcher Yoder, P.C.

(57) ABSTRACT

A system, in one embodiment, includes an optical coherence tomography (OCT) imaging system having a light source configured to emit light. The OCT imaging system further includes a beam splitter configured to receive the light from the light source, split the light into a first light portion directed along a sample arm comprising a sample and a second light portion directed along a reference arm comprising a reference mirror, receive a first reflected light portion from the sample arm and a second reflected light portion from the reference arm, combine the first and second reflected light portions to obtain an interference signal. Further, the OCT imaging system includes a controller having logic configured to perform an auto-ranging process to match the reference arm with the sample arm.

9 Claims, 10 Drawing Sheets

SYSTEM AND METHOD FOR AUTO-RANGING IN OPTICAL COHERENCE TOMOGRAPHY

BACKGROUND OF THE INVENTION

Embodiments of the present invention relate to systems, methods, and devices for imaging and, more particularly, to optical coherence tomography (OCT) imaging techniques.

Optical coherence tomography (OCT) is a non-invasive imaging technique that is often used in clinical applications to obtain high-resolution cross-sectional images of subsurface in vivo (living) biological tissue and other materials. For example, OCT imaging techniques are used in a variety of medical fields, including ophthalmology, cardiology, and dermatology, to name just a few. In particular, OCT imaging is popular in ophthalmology for ocular diagnostic purposes, where it may be used to obtain detailed images of a retina or other structures within a human eye. For instance, OCT imaging has been known to be capable of delineating layers of the retina with a very high degree of clarity. Currently, some OCT imaging techniques are capable of producing images at micrometer, or even sub-micrometer, scale resolutions.

OCT imaging systems operate on the principle of interferometry, in which subsurface light reflections are resolved to provide a tomographic visualization of a sample (e.g., the tissue or object being imaged). Generally, OCT imaging systems split light provided by a light source along a first optical path containing the sample, usually referred to as a "sample arm," and a second optical path containing a reference mirror, usually referred to as a "reference arm." The combination of reflected light from the sample arm and reflected reference light from the reference arm gives rise to an interference pattern, but generally only if light from both arms have traveled the "same" optical distance, wherein "same" means a difference of less than a coherence length. Thus, when acquiring images using an OCT imaging system, an operator may be tasked with ensuring that the reference and sample arms have the same path length, which may involve adjusting the length of the reference arm manually, so that an interference pattern is properly generated. As can be appreciated, due to variations in the size or dimensions of a particular sample type, such as human eyes, the path length of the sample arm may vary, thus requiring the path length of the reference arm to vary to match the sample arm. Moreover, because the path lengths are to be adjusted until they match (e.g., typically with a tolerance of a few millimeters, or even micrometers), this task may not only be difficult to perform accurately, but may also be subject to human error.

Further, once the reference and sample arms are matched, the operator may also be tasked with manually adjusting the focal position of one or more focusing lenses of the OCT system to ensure that the acquired image is in focus. As can be appreciated, manually determining an optimal focusing position may be difficult, particularly when such adjustments are sometimes on the order of micrometers (μm). Moreover, since the focus quality of such adjustments may be subjectively determined based on an operator's vision, what is perceived to be an optimal focus position for the lens may not always correspond to what is actually the optimal focus position. Accordingly, there exists a need for an OCT imaging system that is capable of automating the manual tasks discussed above, thus removing the labor-intensive aspects of OCT imaging while improving the performance and accuracy of OCT imaging systems.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, an optical coherence tomography (OCT) imaging system includes a light source configured to emit light. The OCT imaging system further includes a beam splitter configured to receive the light from the light source, split the light into a first light portion directed along a sample arm comprising a sample and a second light portion directed along a reference arm comprising a reference mirror, receive a first reflected light portion from the sample arm and a second reflected light portion from the reference arm, combine the first and second reflected light portions to obtain an interference signal at a detector. Further, the OCT imaging system includes a controller having logic configured to perform an auto-ranging process to match the reference arm with the sample arm.

In another embodiment, a method for matching a reference arm of an optical coherence tomography (OCT) imaging system to a sample arm of the OCT imaging system includes sweeping the reference arm along a range representative of an uncertainty in the position of a sample in the sample arm, wherein sweeping the reference arm comprises adjusting the path length of the reference arm to each of a plurality of discrete reference arm positions. The method further includes acquiring an axial scan of the sample at each of the discrete reference arm positions, obtaining a composite scan based on all the axial scans, and analyzing the composite scan to determine the position of the sample. Additionally, the method includes selecting the reference arm position corresponding to the determined position of the sample and matching the reference arm to the sample arm by adjusting the reference arm to the selected reference arm position.

In yet a further embodiment, a tangible computer-readable medium having instructions encoded thereon includes code for controlling a reference arm of an optical coherence tomography (OCT) imaging system along a plurality of discrete reference arm positions. The tangible computer-readable medium further includes code for acquiring an image of a sample in a sample arm of the OCT imaging system at each of the discrete reference arm positions. The tangible computer-readable medium also includes code for calculating a figure of merit value from each image, code for selecting a reference arm position having a figure of merit value indicating a match with the sample arm, and code configured to cause the reference arm to be adjusted based upon the selected reference arm position.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention are described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As discussed in detail below, embodiments of the present invention relate to techniques for auto-ranging and auto-focusing in the context of optical coherence tomography imaging. To facilitate a better understanding, the present application is partitioned into three sections, namely a first section that provides a general overview of an optical coherence tomography imaging system, a second section that describes auto-ranging techniques, and a third section that describes auto-focusing techniques.

I. Optical Coherence Tomography Overview

Figure 1:
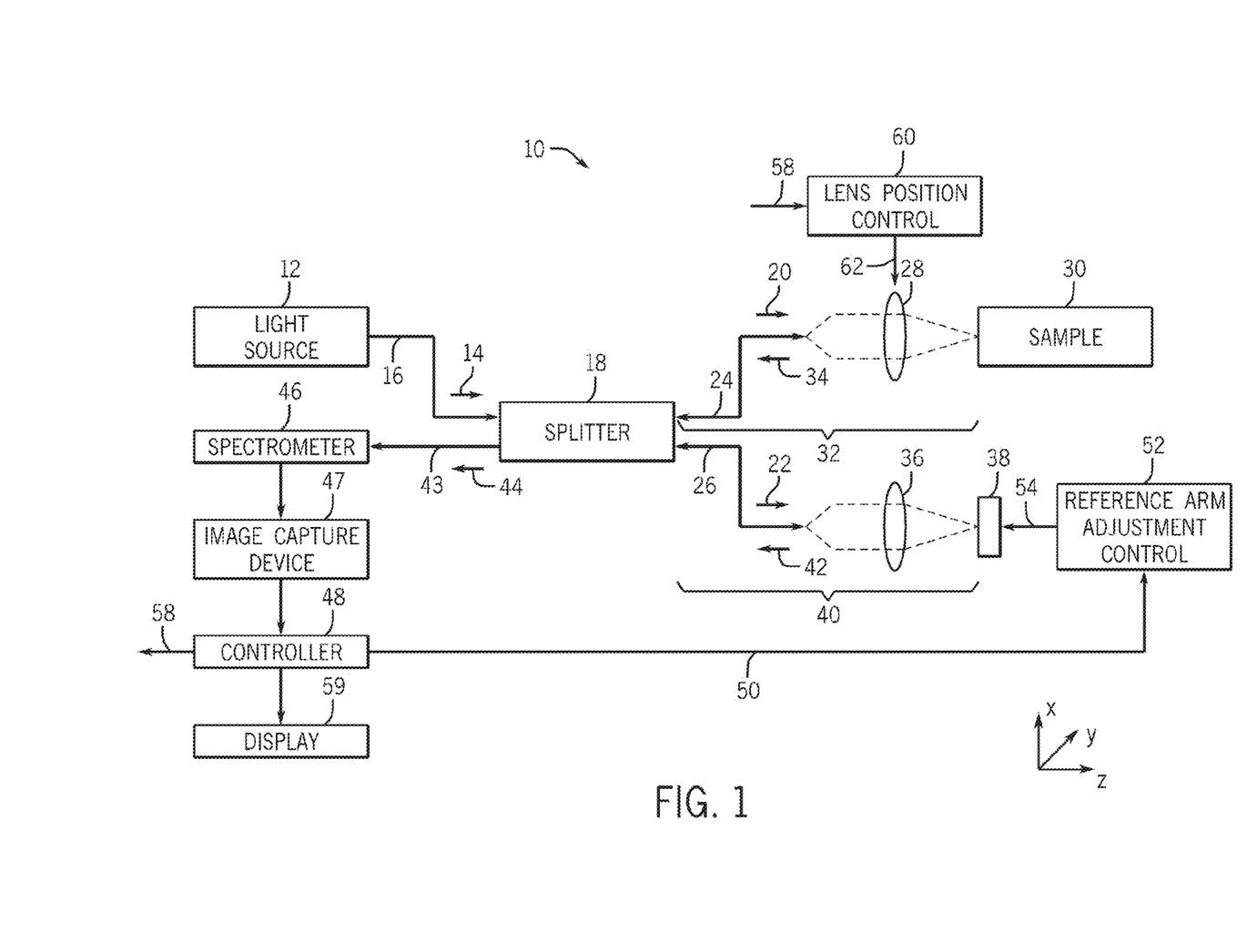
FIG. 1 is a schematic block diagram depicting an optical coherence tomography (OCT) imaging system including a controller configured to provide for auto-ranging and/or auto-focusing functions, in accordance with an embodiment of the present invention.

With the foregoing points in mind, FIG. 1 is a schematic block diagram depicting an optical coherence tomography (OCT) imaging system 10, in accordance with embodiments of the present invention. Particularly, as will be discussed in further detail below, the OCT imaging system 10 may be configured to perform auto-ranging to match a reference arm with a sample arm and/or auto-focusing to adjust a focusing lens in the sample arm to an optimal focal position.

As noted above, OCT is an imaging technique that operates based on the principle of interferometry, wherein light reflections from a sample and a reference point are resolved to generate an interference pattern that may be used to obtain a tomographic visualization of the sample, such as biological tissue. For example, OCT imaging systems, such as the system 10, may split light provided by a light source to a sample arm and a reference arm. The reflected light from the sample and the reflected light from the reference, which may be a mirror, are combined or superimposed to obtain an interference pattern. OCT imaging is both popular and useful, particularly in the field of ophthalmology and ocular diagnosis, as the imaging techniques allows for non-invasive imaging of sub-surface tissue, such as the retina of a human eye. Indeed, OCT imaging has been key in the early detection of certain ocular ailments, such as diabetic retinopathy and macular degeneration.

As shown in FIG. 1, the OCT imaging system 10 includes a light source 12 that may provide light 14 along a pathway 16 to a beam splitter 18. By way of example, the light source 12 may be a broadband light source, such as a super-luminescent diode (SLD), mode-locked laser (e.g., a $TiAl_2O_3$ mode-locked laser), or an edge emitting LED. In one embodiment, the light source 12 may be configured to emit near-infrared light (e.g., having a wavelength ($\lambda$) of between approximately 800 to 1000 nanometers). The pathway 16 may be made of material configured to transmit light, such as an optical fiber.

The beam splitter 18 may be configured to split the light 14 into two portions, referred to in FIG. 1 as light portion 20 and light portion 22. In certain embodiments, the beam splitter 18 may be an interferometer, such as a Michelson interferometer. Light portion 20 may be guided along pathway 24 through a lens 28 to a sample 30, which is a target that is being imaged. For instance, in a medical imaging application, the sample 30 may be organic tissue, such as a human eye. In other applications, such as art conservation applications the sample 30 may also be an inorganic object (e.g., layers of a painting). As indicated in FIG. 1, the path along which light portion 20 is transmitted may be referred to as the sample arm 32. The light portion 22 is similarly guided along pathway 26 through another lens 36 to a reference mirror, represented here by reference number 38, which may collectively form the reference arm 40. As can be appreciated, the pathways 24 and 26, like the pathway 16, may also include optical fibers configured to transmit light.

As further shown in FIG. 1, the light portion 22 is reflected from the reference minor 38 to form light portion 42, and the light portion 20 is reflected from the sample 30 to form light portion 34. Light portion 42 and light portion 34 are guided back to the beam splitter 18 by the pathways 26 and 24, respectively. The beam splitter 18 may combine the reflected light portions 34 and 42 to form the superimposed light beam 44, which may represent an interference signal. As can be appreciated, most of the light 20 directed at the sample 30 scatters, which typically leaves only a small portion reflecting from sub-surface features of interest. Based on the principle of optical coherence, only the reflected (e.g., non-scattered) light is coherent and detected by the beam splitter 18. Further, as will be appreciated, the scattered light, which may normally contribute to glare, may be filtered out. For example, a beam splitter, such as an interferometer, may be configured to detect only coherent light.

The interference signal 44 may be guided to a spectrometer 46 by the pathway 43 (e.g., an optical fiber), and then be analyzed by the spectrometer 46 and the image capture device 47 to determine depth and opacity information. For instance, the interference signal 44 may be spectrally dispersed by the spectrometer 46 into spatially separate light portions according to different wavelength ranges. These separated light portions may be detected by the image capture device 47, which may include a charge-coupled device (CCD) or CMOS sensor with multiple pixels, a line scanning camera, or a combination thereof, to detect the intensities represented by each separate light portion. This data may then be provided to the controller 48, which may apply one or more digital signal processing steps to computationally translate the data into a viewable image for viewing on the display 59. The process may involve receiving and processing the intensity information to derive depth information using Fourier transformations of the spectra representing the separated light portions, as determined by the spectrometer 46. For example, the interference signal may be detected in the spectral domain, and then inverse Fourier transformed to the time domain, which may result in a signal that provides sample reflectivity as a function of depth. This type of optical coherence tomography imaging may be referred to spectral domain OCT (SD-OCT) or Fourier domain OCT. When compared to other OCT techniques, such as time-domain OCT, spectral domain OCT generally allows for higher resolution images, higher scan rates, and improved signal-to-noise ratio. However, it should be appreciated, that the techniques related to auto-focusing and auto-ranging, as discussed below, may be applied to either of these OCT techniques. In a further embodiment, spectral domain OCT imaging may be implemented by using a narrow band light source in which the frequency is swept rapidly in time across a broad tuning range, with the interference signal being collected at each frequency while the swept source is tuned.

As discussed above, in order to properly measure the interference between the light 34 reflected from the sample 30 and the light 42 reflected from the reference minor 38, the path lengths of the sample arm 32 and the reference arm 40 should be matched such that any difference between the path lengths is less than a coherence length. By way of example, if a typical OCT imaging system is configured to capture an image across a 2 to 3 millimeters of depth (e.g., a "minimum depth"), the path length of the sample arm 32 and the reference arm 40 much match to within this distance. Moreover, variations in the sample 30 may add additional uncertainty to the sample position. For instance, if the sample is a human eye, the human eye may, on average, have an axial length that varies from between 22 to 30 millimeters, which adds a degree of uncertainly of 8 millimeters. Further, depending on the characteristics of a patient's head and/or face, as well as how the patient is positioned, additional uncertainty may exist. For instance, these factors may inject up to another 10 millimeters of uncertainty. Thus, in light of this potential large range of uncertainty, it may be difficult for conventional OCT imaging systems to locate where, in the axial direction, the minimum depth (e.g., a 2-3 millimeter range) in which the sample 30 resides.

To address these issues, the controller 48 of the OCT imaging system 10 of FIG. 1 may be configured to implement an auto-ranging function to automatically match the path length of the reference arm 40 to that of the sample arm 32. As discussed in more detail below, the OCT imaging system 10 includes a mechanism 52 for adjusting the path length of the reference arm 40. For instance, the mechanism 52 may be mechanical in nature, such as one or more rapid scanning optical delay (RSOD) lines. This allows for the length of the reference arm 40 to be adjusted in discrete steps, wherein an axial scan may be acquired at each step along a range of the total adjustment length to construct a composite long depth range scan. For each discrete reference arm position, the corresponding scan is analyzed to determine one or more figures of merit (FOM), with the controller 48 searching for the position in which the FOM is at a maximum (or a minimum depending on the metric being used). Once the correct position (e.g., one that matches the sample arm) is found, the controller 48 provides the signal 50 indicating the correct position to the reference arm control mechanism 52. The control mechanism may then output the control signal 54, which may cause the reference arm to be adjusted to the selected position indicated by the signal 50. In one embodiment, the control mechanism may include a servo control. This process will be discussed in more detail below in Section II. In some embodiments, the adjustment of the reference arm to vary the path length may include an angular adjustment, such as to the reference mirror 38. The magnitude of each discrete step may be equal or unequal.

Next, once the reference arm has been adjusted to the position selected by the controller 48 in response to the auto-ranging function, the sample 30 may still need to be focused by adjusting the position of the lens 28 to an optimal focal position. Accordingly, the controller 48 of the present embodiment may also be configured to implement an auto-focusing function. As discussed in more detail below, the OCT imaging system 10 includes a lens position control mechanism 60 that may be configured to adjust the focal position of the lens 28. To determine the focal plane of the sample 30, the controller 48 may acquire an OCT image at each of various focal positions of the lens 28. Each image may then be analyzed by the controller 48 to determine one or more quantitative FOMs at each depth position. A model is then mathematically fitted to the FOM data, wherein the point corresponding to either a minimum or maximum (depending on the FOM used) corresponds to the optimal focal position. Once the optimal focal position is found, the controller 48 provides the signal 58 indicating the focal position to the lens control mechanism 60. Based on the signal 58, the lens control mechanism 60 may output the control signal 62, which may cause the lens 28 to be adjusted to the focal position indicated by the signal 58. In one embodiment, the control mechanism 60 may include a motorized actuation system. This auto-focusing process will be discussed in more detail below in Section III.

Figure 2:
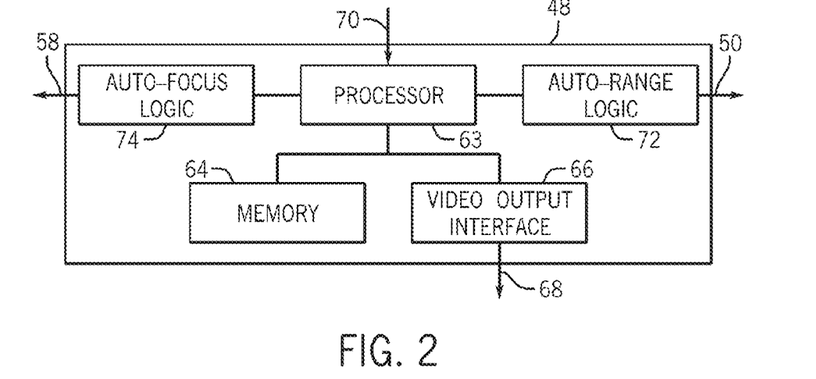
FIG. 2 is a block diagram illustrating the controller of FIG. 1 in more detail, in accordance with an embodiment of the present invention.

FIG. 2 is a block diagram depicting a more detailed view of the controller 48, in accordance with an embodiment of the present invention. The functional blocks depicted in FIG. 2 may include hardware elements (e.g., circuitry), software elements (e.g., computer code stored on computer-readable media, such as a hard drive or system memory), or a combination of both hardware and software elements. As shown, the controller 48 may include a processor 63, memory device 64, and video output interface 66.

The processor 63 may generally be configured to control the functions of the controller 48, and thus of the OCT imaging system 10. For instance, the processor 63 may provide the processing capability to analyze and process the data captured by the image capture device 47, referred to herein by reference number 70. For example, as discussed above, the interference signal 44 may be detected in the spectral domain, and then inverse Fourier transformed to the time domain, which may result in a signal that provides sample reflectivity as a function of depth. The processor 63 may thus be configured to apply such transformations between the spectral and time domains in order to extract depth and intensity information in order to generate viewable OCT images. The OCT image(s) may be stored in the memory device 64 and/or sent to the display 59 (FIG. 1) by way of the video output interface 66 as image data 68. For example, the interface 66 may include any suitable type of display interface, such as a VGA, DVI, HDMI, or DisplayPort interface. The display 59 may be any type of display suitable for displaying a computer image, such as a cathode-ray tube (CRT) display, an LCD display, or an organic LED (OLED) display. In some embodiments, the processor 63 may also be configured to provide post-processing functions on the digital OCT images, such as to enhance them for aesthetic purposes to potentially enable a medical professional to more easily review and reach a diagnosis. By way of example only, such post-processing functions may include noise reduction/removal, brightness/contrast adjustments, sharpening, and so forth.

The processor 63 may also be configured to operate in conjunction with the auto-range logic 72 and the auto-focus logic 74 to provide the above-mentioned auto-ranging and auto-focusing functions, as will be discussed further below. In the illustrated embodiment, the processor 63 may include one or more microprocessors, such as one or more general-purpose microprocessors, application-specific microprocessors (ASICs), digital signal processors, or a combination of such processing components.

The memory device 64 may include volatile memory, such as random access memory (RAM), or non-volatile memory, such as read-only memory (ROM), hard disk drive, or flash memory, or a combination of RAM and ROM devices. For example, the memory device 64 may store OCT images generated by the processor 63, which may be stored for later viewing. Though not shown in FIG. 2, in some embodiments, the controller 48 may include communication circuitry, such as a networking interface, enabling the controller 48 to send OCT image data to other devices. For instance, in such embodiments, OCT images acquired by the system 10 may be sent to other devices for storage, such as a patient database system, such as a picture archive and communication system (PACS), or may be sent to other devices for diagnostic purposes. The memory 64 also stores instructions or data to be processed by the processor 63, which may include instructions for processing the data 70, and for performing auto-ranging or auto-focusing functions. Further, when performing auto-ranging and/or auto-focus functions, the acquired images on which FOMs are determined may be stored in the memory device 64.

II. Auto-Ranging Techniques

As discussed above, natural variations in a particular type of sample 30, such as the human eye, may make it challenging to locate the position of the sample 30 in order to match the reference arm 40 with the sample arm 32. By way of example only, a human eye may have an axial length that varies from between 22 to 30 millimeters, which adds a degree of uncertainly of approximately 8 millimeters. Thus, if it is the retina of the eye that is to be imaged, there may be an 8 millimeter window of uncertainty. That is, the retina of the eye is likely located somewhere within that window. Further, based on variations in a patient's facial structure and/or how the patient positions their head, additional uncertainty, i.e., up to an additional 10 millimeters, may be present. For instance, using these example values, there may be an 18 millimeter window of uncertainty in which the sample 30, i.e., the patient's eye, is located in the sample arm 32. In some embodiments, the window of uncertainty may be between approximately 5 to 30 millimeters. Since the reference arm 40 and the sample arm 32 should be matched in order to properly measure the interference between the reflected light portions 34 and 42, the controller 48 may initially perform the auto-ranging function described above to determine the position of the sample 30 and to adjust the reference arm 40 accordingly.

To implement the auto-ranging function discussed above, the controller 48 may essentially sweep the reference arm position along a number of discrete positions that define a range that covers at least the window of uncertainty. By way of example, if the OCT imaging system 10 is configured to capture an image across 2 to 3 millimeters of depth (e.g., a "minimum depth"), each discrete position of the reference arm 40 within the sweep may cover at least a different portion of the window of uncertainty. Using the reference arm control mechanism 52, the reference arm 40 may then be adjusted to each of the discrete positions covering the window of uncertainty, wherein, at each discrete step, a short range (e.g., 2-3 millimeters in depth) axial scan are obtained. Once the short range axial scans for each discrete step is obtained, the controller 48 may process these short range axial scans to determine a composite long range scan covering the window of uncertainty.

Next, the composite scan is analyzed by the controller 48 (e.g., via processor 63) to determine the region in which the sample 30 resides. In one embodiment, the processor 63 may calculate one or more figures of merit (FOM) at each of the discrete reference arm positions. Based on the FOMs, the controller 48 may determine where a maximum or minimum occurs, which may indicate the reference arm position that is matched with the sample arm 32, thereby giving the position of the sample.

Figure 3:
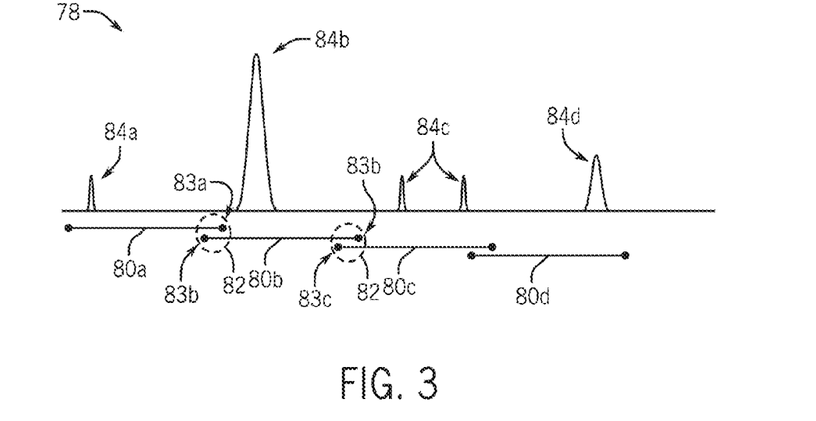
FIG. 3 illustrates a composite scan that may be determined during an auto-ranging process, in accordance with an embodiment of the present invention.

This process may be better understood with reference to FIG. 3, which shows a graph illustrating an example of a composite scan 78 derived from short range scans at each discrete reference arm position during the auto-ranging sweep along a z-axis in the reference arm 40. For instance, the present figure shows, by way of example, four discrete reference arm positions 80*a*-80*d*, although other embodiments may include fewer or more reference arm positions 80 depending on the depth of the window of uncertainty and/or the minimum depth that the OCT imaging system 10 is configured to capture an image. In the present embodiment, it should be noted that adjacent reference arm positions may slightly overlap at their boundaries 83, as indicated by reference number 82, although other embodiments may omit this feature.

For each short range scan (e.g., corresponding to a single reference arm position), one or more FOMs are determined. By way of example, an FOM may include the peak intensity of the signal, the total integrated intensity of each scan, a thresholded intensity, as well as various measures of sharpness similar to those used in microscopy applications, such as entropy and/or moment about a mean. Additionally, analysis of features unique to a sample 30, such as reflections from structural features of the sample 30, may also be a basis for deriving an FOM. Further, the analysis may include a single FOM, or a combination of FOMs (multiplied together or otherwise mathematically combined), which may improve accuracy. Referring still to FIG. 3, reference numbers 84 represent FOM(s) determined with respect to each axial scan. By way of example only, the FOM 84 may be based upon reflection from structural features of the sample 30.

As shown in FIG. 3, the FOM 84*b* within the portion of the composite scan 78 corresponding to the reference arm position 80*b* has the highest value. Thus, the controller 48 may identify the reference arm position 80*b* as the position in which the reference arm 40 matches the sample arm 32. Accordingly, the controller 48 sends the signal 50 indicating the correct position to the reference arm control mechanism 52, which may then actuate the reference arm 40 (e.g., using a servo mechanism) to cause it to adjust to the indicated position. In other words, the analysis of the reference arm sweep process essentially acts as a feedback loop to bring the reference arm 40 to a position that matches the sample arm 32 of FIG. 1. By way of example only, in one embodiment, the reference arm control mechanism 52 may include one or more rapid scanning optical delay (RSOD) lines having a grating, such as a diffraction grating, wherein the adjustments may be translated into angular motion of either the reference minor 38 or the grating, or both. In additional embodiments, rather than using a control mechanism, the OCT imaging system 10 may include multiple reference arms, and the interference signal may be distinguished using frequency encoding or by switching between the reference arms. For instance, in such embodiments, the matching reference arm is selected from the multiple reference arms, as opposed to manipulating the path length of the reference arm. As can be appreciated, the auto-ranging functions discussed above may generally be performed by the processor 63 in conjunction with the auto-range logic 72 shown in FIG. 2.

Figure 4:
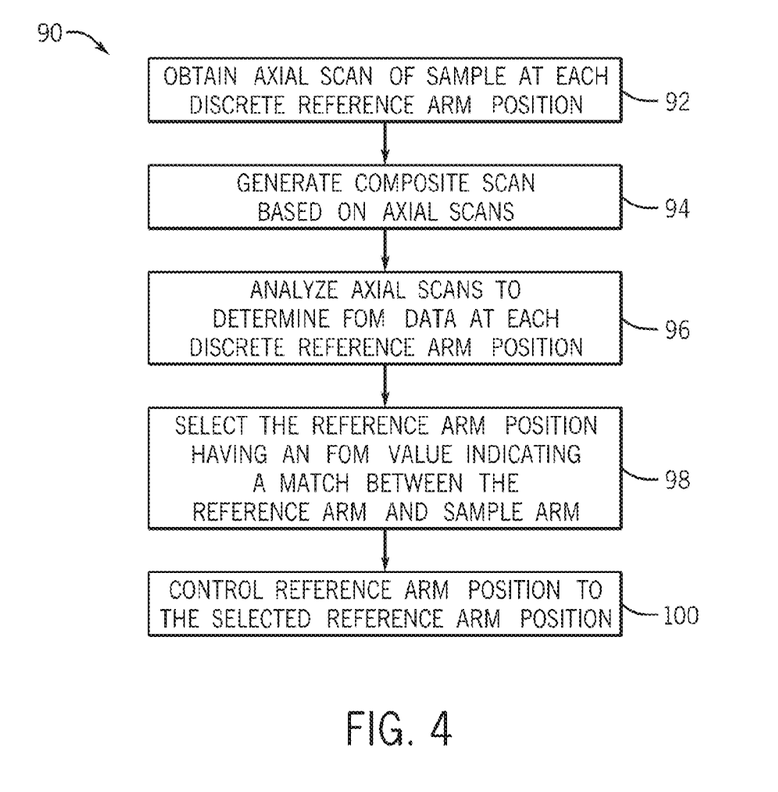
FIG. 4 is a flow chart depicting a process for auto-ranging to match a reference arm with a sample arm, in accordance with an embodiment of the present invention.

FIG. 4 is a flowchart that illustrates the auto-ranging process 90 described above with reference to FIG. 3 that may be performed by the controller 48 of the OCT imaging system 10 of FIG. 1. As shown, the process 90 begins at step 92, where an axial scan of the sample 30 is obtained at each discrete reference arm position during an auto-ranging sweep. As discussed above, the sweep is configured such that it at least encompasses the window of uncertainty defined by variations of sample dimensions (e.g., variability in eye axial length) and/or natural patient variations (e.g., variations in patient face and/or head structure).

Thereafter, at step 94, a composite scan (e.g., 78) is derived based on the axial scans obtained at step 92. The controller 48 of the OCT imaging system 10 may then analyze the composite scan 78 to determine at least one figure of merit (FOM) at each discrete reference arm position (e.g., 80a-80d), as indicated at step 96. Next, at step 98, the reference arm position that contains an FOM value that indicates the nominal position of the sample 30 is selected. For instance, the selected reference arm position may have an FOM value that is a maximum (or minimum depending on the FOM used). The selected reference arm position may match the sample arm path length at least within a coherence length, as discussed above. Finally, once the matching reference arm position is determined, the process 90 continues to step 100, and the reference arm 40 is controlled (e.g., by the control mechanism 52) to the selected position.

III. Auto-Focusing Techniques

Before discussing the auto-focusing techniques of the present disclosure in detail, it should be noted that some conventional OCT imaging systems lack any sort of auto-focusing mechanism. As discussed above, such conventional systems rely on manual focusing by an operator, which may be subject to inaccuracies due at least in part to human error. Moreover, some conventional OCT imaging systems may use a low transverse resolution for a large depth-of-field, which assumes that a sample is sufficiently in focus at any position in depth. However, image contrast and resolution along the depth (e.g., z-direction) are still dependent upon the position of a focusing lens relative to a sample and, therefore, it may be useful to provide a technique for automatically determining an optimal focal position and bringing the focusing lens to that position, as discussed in more detail below.

Figure 5:
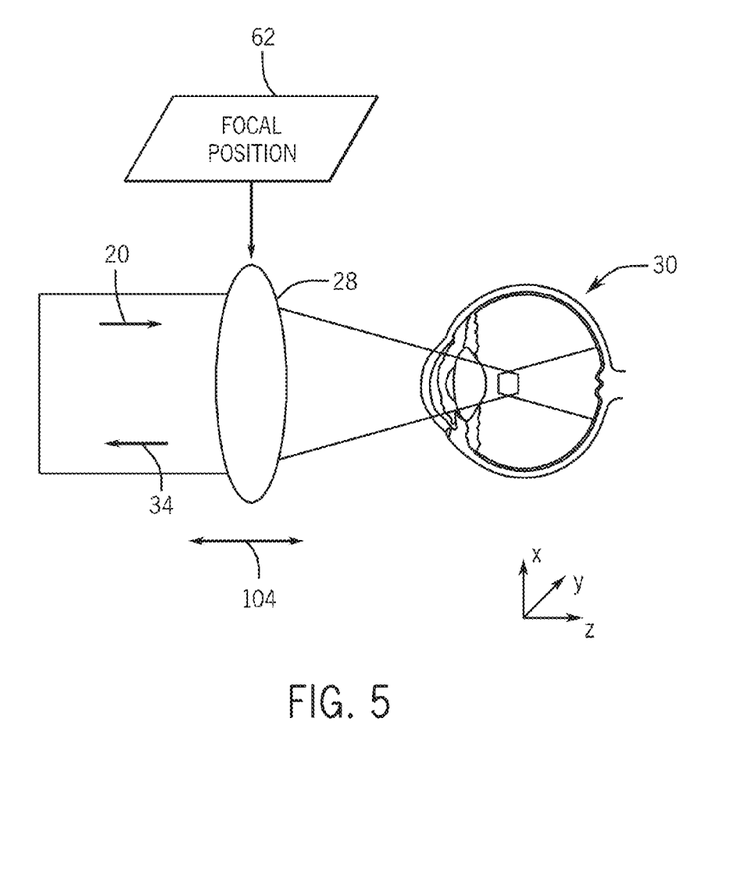
FIG. 5 is a more detailed view showing how a focusing lens within the sample arm may be adjusted, in accordance with an embodiment of the present invention.

Once the reference arm 40 and the sample arm 32 are matched for OCT purposes, the controller 48 may perform an auto-focusing function in order to adjust the lens 28 within the sample arm 32 to a position that provides optimal focus with respect to the sample 30. For instance, a more detailed view of a portion of the sample arm 32 is illustrated in FIG. 5, which depicts an example in which the sample 30 is a human eye. As discussed above, OCT imaging is generally considered to be particularly well suited to ocular diagnosis due to its ability to capture high resolution images of layers of the retina and the cornea, as well as its non-invasiveness. For instance, OCT imaging is often used for early detection of various ocular diseases, such as glaucoma, diabetic retinopathy and macular degeneration (e.g., cystoid macular edema), among others.

As shown in FIG. 5, the light portion 20 provided by the beam splitter 18 may be focused by the lens 28, directed to the sample 30, in this case an eye, and reflected as light portion 34. Whether or not the sample 30 will appear to be in focus in the resulting OCT image may depend on the focal position of the lens 28. For instance, if the lens 28 is too close or too far from the sample 30, the resulting OCT image may be out of focus and may not be suitable for diagnostic purposes. Accordingly, the auto-focusing process that may be performed by the controller 48 of the OCT imaging system 10 may determine an optimal focal position and adjust the position of the lens 28 in the directions 104 (e.g., the ±z-direction) accordingly.

The process by which the controller 48 may perform the auto-focusing process of the present disclosure may be similar in some aspects to the auto-ranging process described above in Section II. For instance, the auto-focusing process generally includes sweeping the lens 28 along a range of available discrete focal positions within the sample arm 32. At each discrete focal position, an image is acquired, and the processor 63 may determine one or more quantitative figures of merit (FOM) for each image at each discrete focal position. For example, in one embodiment, a FOM may be a width of autocorrelation function, which may be generated by the self-interference of light scattered from the sample only. In this embodiment, since the self-interference spectrum contains only low-frequency components, image acquisition speed may be increased by binning some number of pixels (e.g., 2×2 binning) or by using a line scan camera with a smaller number of pixels.

In other embodiments, the FOM extracted from auto-focusing images may include a mean or average image intensity, a Brenner gradient, and image intensity (variance), to name just a few. Further, the FOM may also be a combination of two or more independent FOMs. For instance, in one embodiment, the FOM may be the product of a Brenner gradient FOM and a variance FOM. After calculating a chosen FOM, a mathematical model is applied to fit a function (e.g., a curve) to the FOM data with respect to focal position (depth). By way of example, the mathematical model may be determined empirically depending upon the particular FOM of choice, as well as based upon characteristics of the focusing lens, illumination, etc. In some embodiments, the best fit may at least partially be determined based on any one of a number of mathematical regression techniques. As can be appreciated, one goal may be to select a model that uses the fewest number of fitting parameters, and thereby requires the fewest number of images possible, which may speed up the auto-focusing process. The maximum (or minimum) of the fitted function is taken as the optimal focal position and may be provided to the lens position control mechanism 60 to bring the sample 30 into focus.

Figure 6A:
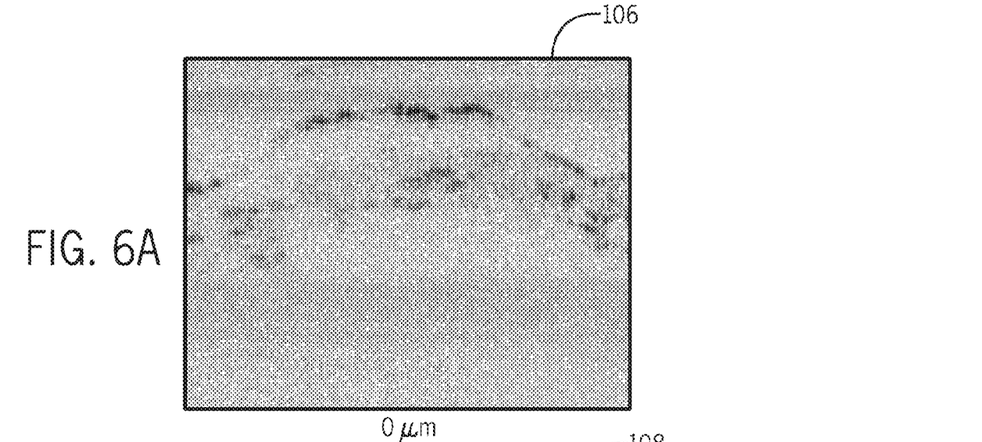
FIGS. 6A-6I illustrate images of a sample that may be obtained at various focal positions during an auto-focusing process, in accordance with an embodiment of the present invention.
Figure 6B:
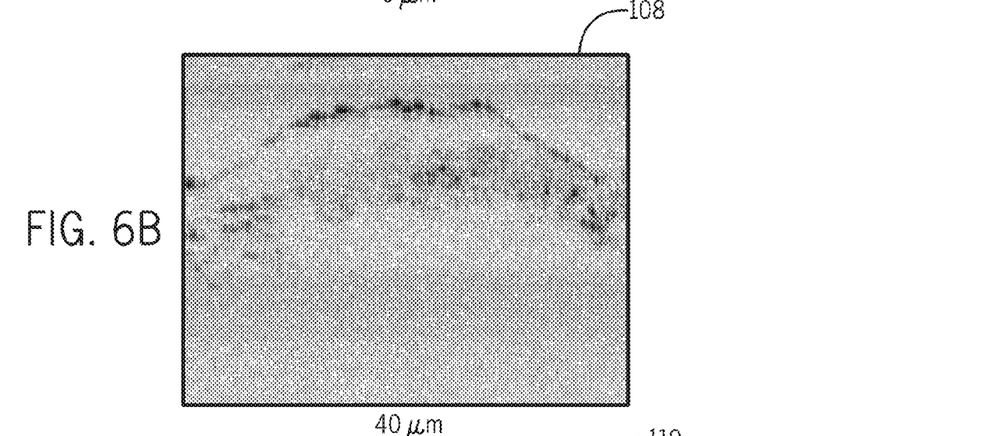
Figure 6C:
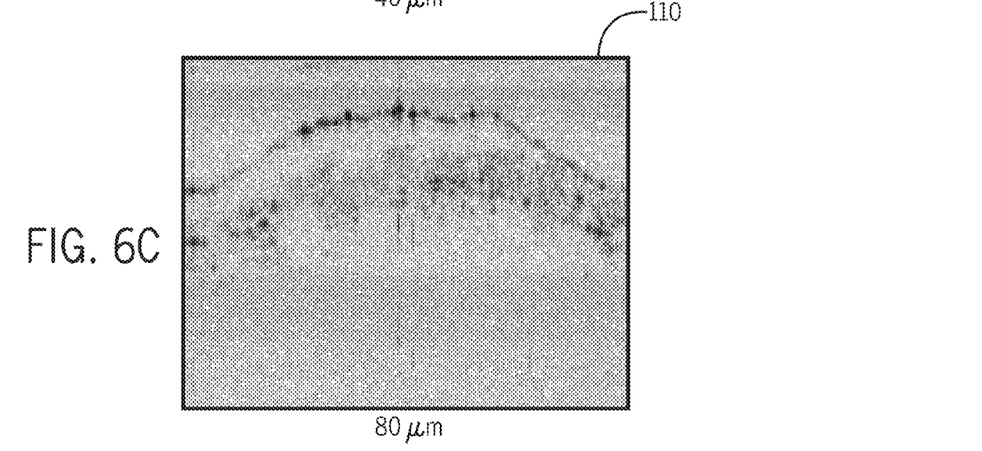
Figure 6D:
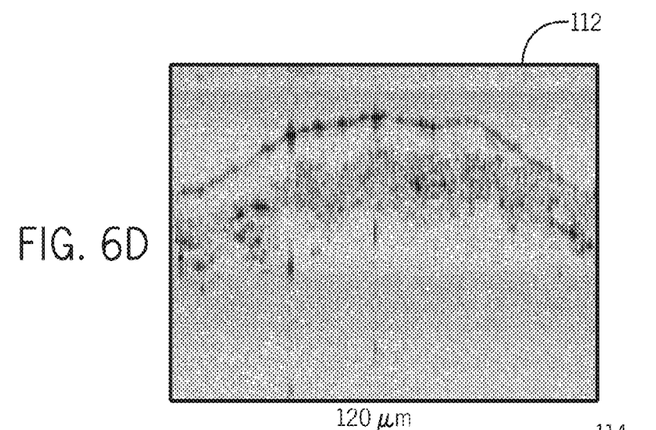
Figure 6E:
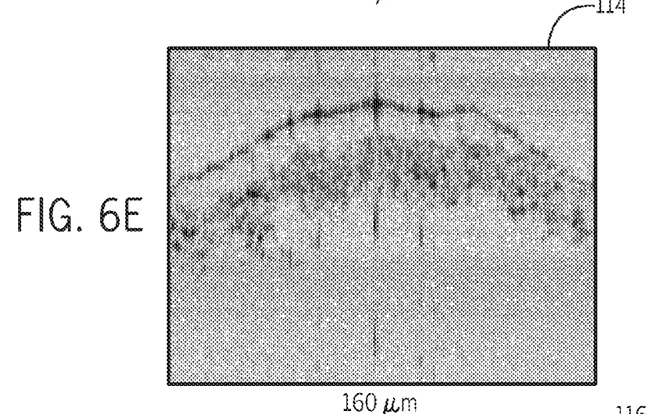
Figure 6F:
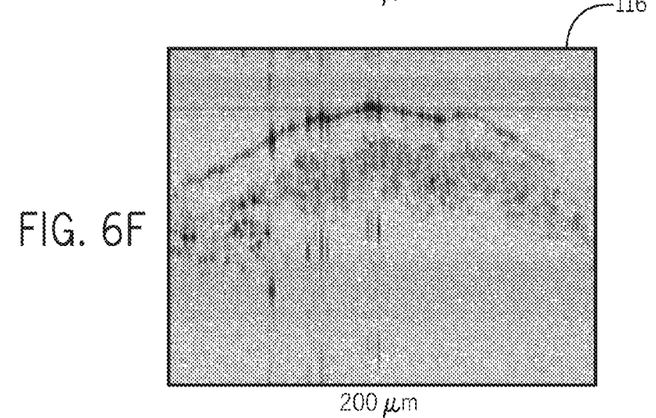
Figure 6G:
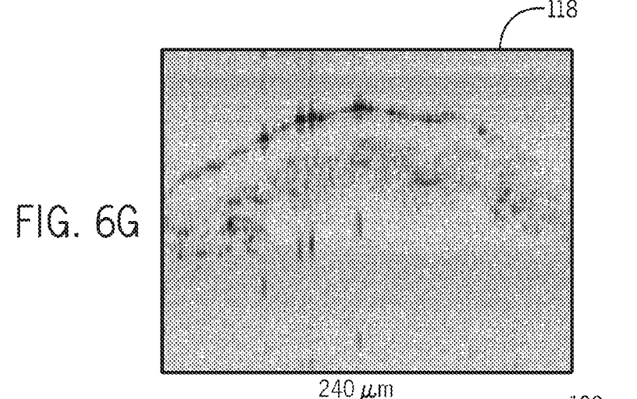
Figure 6H:
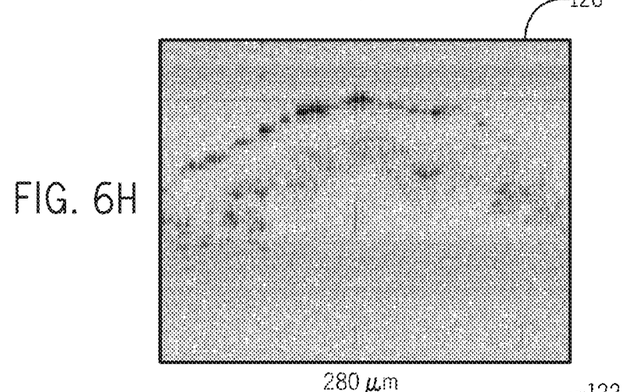
Figure 6I:
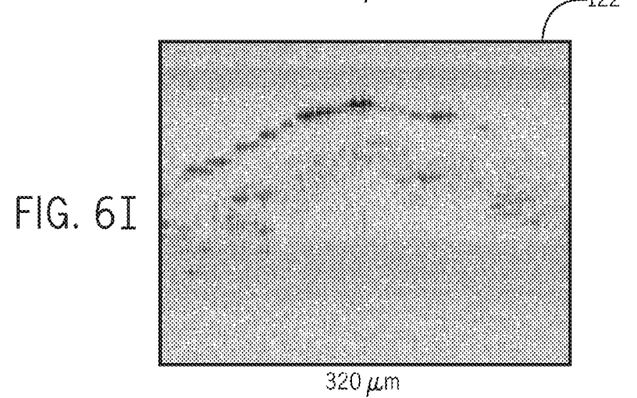

To provide a more illustrative example, FIGS. 6A-6I illustrate images acquired at various focal positions along the depth of the sample arm 32 using a slice of an onion as the sample 30. For instance, FIG. 6A illustrates an image 106 acquired at a first focal position of 0 μm, which may represent the starting position of the range along which the auto-focusing sweep of the lens 28 occurs. FIG. 6B illustrates an image 108 acquired at a second focal position that is 40 μm offset from the first focal position. FIG. 6C illustrates an image 110 acquired at a third focal position 80 μm away from the first position. FIG. 6D illustrates an image 112 acquired at a fourth focal position 120 μm away from the first position. FIG. 6E illustrates an image 114 acquired at a fifth focal position 160 µm away from the first position. FIG. 6F illustrates an image 116 acquired at a sixth focal position 200 µm away from the first position. FIG. 6G illustrates an image 118 acquired at a seventh focal position 240 µm away from the first position. FIG. 6H illustrates an image 120 acquired at an eighth focal position 280 µm away from the first position. Finally, FIG. 6I illustrates an image 122 acquired at a third focal position 320 µm away from the first position. As can be seen, the images 106-122 are at varying degrees of focus. In the present example, the step size between each focal position in the auto-focus sweep is set to 40 µm. However, it should be appreciated that this step size may be increased or decreased in other embodiments to provide for fewer or more images (e.g., a larger step size results in less image samples, and a smaller step size results in more images samples across the same sweep depth).

Figure 7:
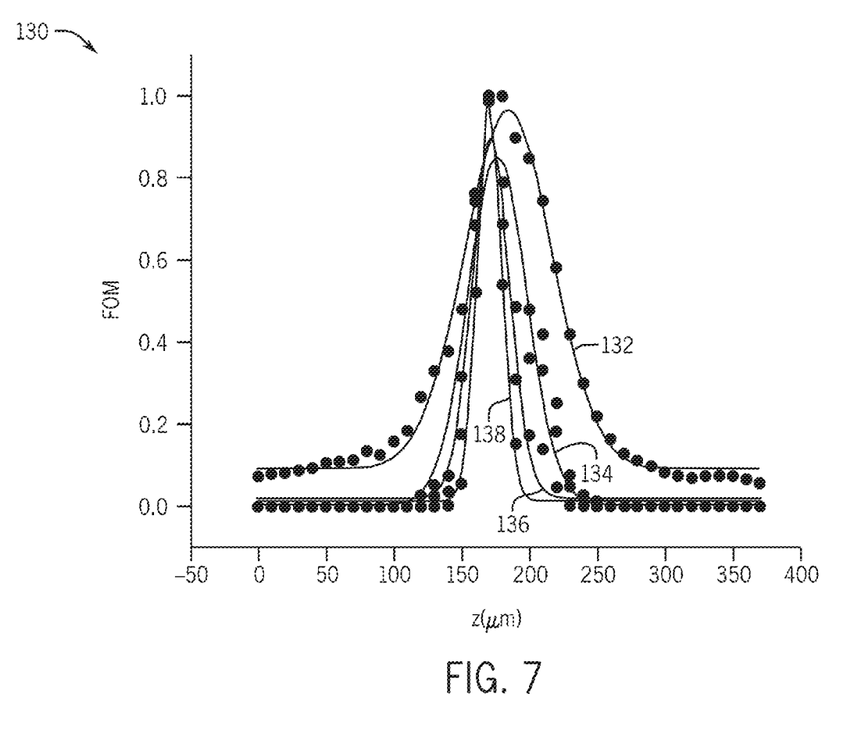
FIG. 7 is a graph depicting several examples of figures of merit (FOMs) that may be used to determine an optimal focal position for a lens in a sample arm of an OCT imaging system, in accordance with an embodiment of the present invention.

Next, the images 106-122 would be analyzed by the controller 48 to obtain a chosen figure of merit. For instance, a best-fit curve would be determined based on the FOM data with respect to focal position (depth). Referring to FIG. 7, a graph 130 is provided showing examples of several FOM data sets and their respective fitted curves in accordance with embodiments of the present invention. For instance, curve 132 represents a mathematical model fitting FOM data based on average image intensity (mean). Curve 134 may represent a mathematical model fitting FOM data based on a Brenner gradient. By way of example, the Brenner gradient may be determined based upon the following expression:

$$F_{Brenner} = \Sigma_{Height}\Sigma_{Width}((i(x+n),y) - i(x, y))^2, \quad (1)$$

wherein i represents the intensity of a given pixel within an image, n represents a small integer (e.g., n=2), and x and y represent pixel coordinates of the image. Generally, the Brenner gradient may, for each pixel in a captured image, compute a difference in intensities between each respective pixel and a neighboring pixel laterally separated from the pixel by at least one other pixel, and sum different intensities for each pixel across the height and width of the image. Curve 136 may represent a mathematical model fitting FOM data based on variance, and curve 138 may represent a mathematical model fitting FOM data based on the product of the Brenner gradient and variance.

Regardless of the FOM metric used, it should be understood that analysis of the fitted mathematical model is then performed to determine a maximum (or a minimum in some cases). As can be seen in FIG. 7, depending on the FOM used, a maximum occurs at between approximately 175-200 micrometers. Indeed, referring back to the samples images of FIGS. 6A-6I, the image 114 at 160 µm (FIG. 6E) and 116 at 200 µm (FIG. 6F) appear to be the most in focus. The optimal focal position may thus be determined as the position closest to the maximum (or minimum) of the fitted curve that lens 28 is capable of achieving. For instance, even though the step size during the auto-focus sweep may be set to 40 µm, it should be appreciated that the lens control mechanism 60 may be configured to have a minimum step resolution for adjusting the lens 28 at smaller intervals (e.g., 1 µm, 2 µm, 5 µm, 10 µm, etc.). On the other hand, if the minimum step resolution of lens step size is unable to reach the exact focal position indicated by the fitted curve, the controller 48 may instruct the lens control mechanism 60 to position the lens 28 to the closest possible focal position, i.e. via servo control.

In another embodiment, the selected FOM may be the inverse of the Brenner gradient. As will be appreciated, a Brenner gradient function may be approximated using a Lorentzian function, which is given by:

$$F(z) = \frac{a}{(z-z_0)^2 + b} \quad (2)$$

Figure 8:
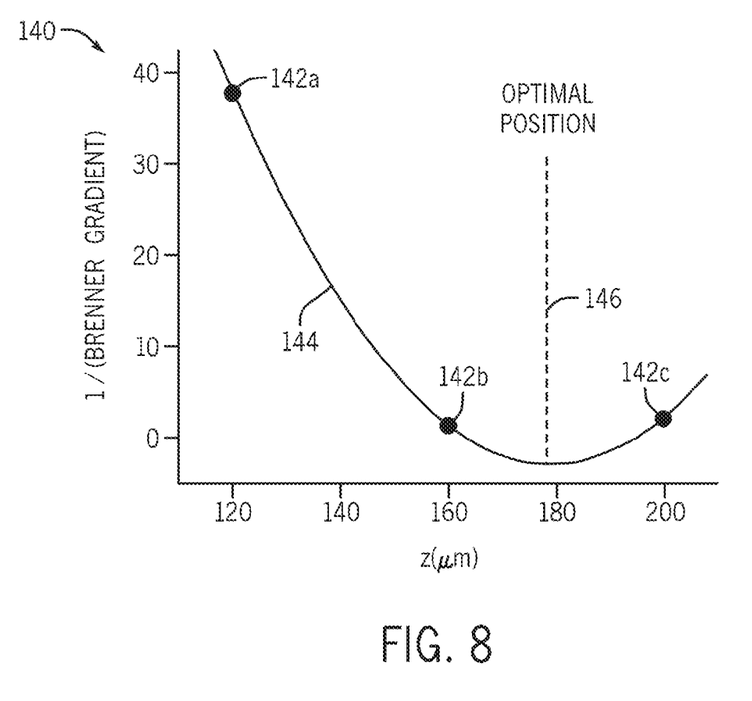
FIG. 8 is a graph illustrating the use of an FOM that includes the inverse of a Brenner gradient, in accordance with an embodiment of the present invention.

As can be seen the Lorentzian function is essentially the reciprocal of a quadratic function. Therefore, the inverse of the Brenner gradient may be fitted using a second-order polynomial, which may be determined by as few as three images. For instance, FIG. 8 shows a graph 140 depicting an embodiment in which the FOM used for auto-focusing is based on an inverse of the Brenner gradient. As shown here, based on FOM values 142a, 142b, and 142c, from three sample images, the second-order polynomial function 144 may be determined and fitted to the data points 142a-142c. Accordingly, in this example, the controller 48 is configured to locate a minimum, as indicated by reference number 146, corresponding to the optimal focal position. As can be appreciated, in such an example, depending on the distance of the auto-focusing sweep, it may be useful to select three focal positions that are evenly distributed across the sweep distance so that at least one sample is obtained on either side of the optimal focal position.

Figure 9:
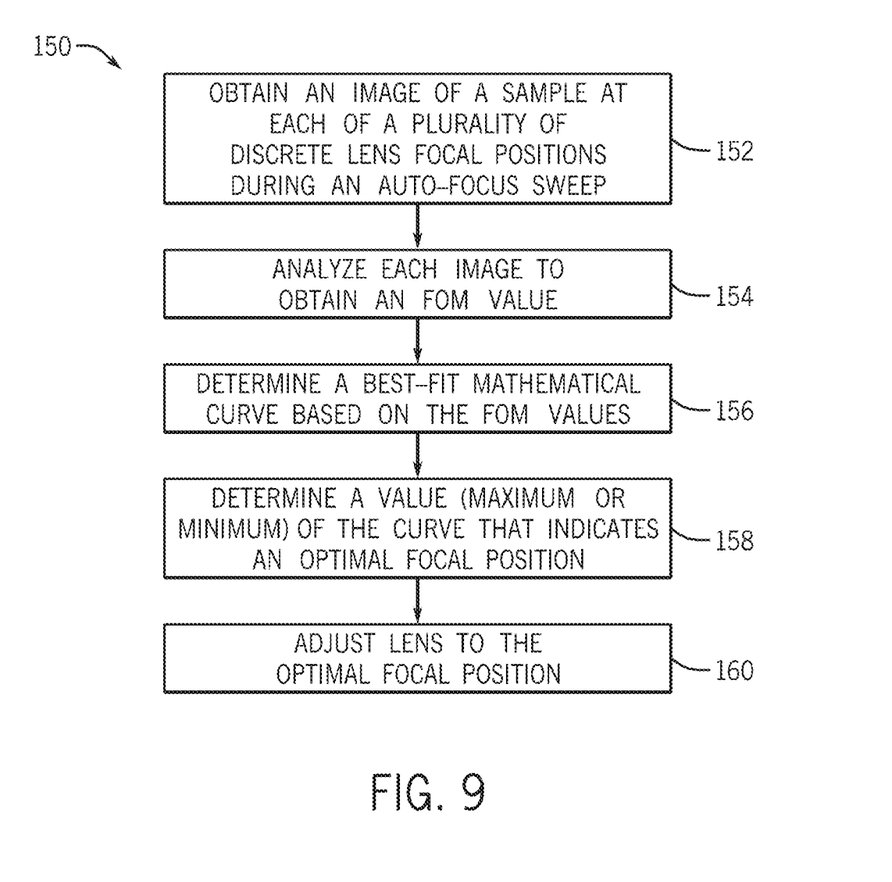
FIG. 9 is a flow chart depicting a process for auto-focusing, in accordance with an embodiment of the present invention.

FIG. 9 is a flow chart that illustrates the auto-focusing process 150 described above with reference to FIGS. 5-8. The auto-focusing process 150 may be performed by the controller 48 (e.g., via the processor 63 and auto-focus logic 74) of the OCT imaging system 10 of FIG. 1. As shown, the process 150 begins at step 152, wherein the lens 28 of the sample arm 32 is adjusted to each of multiple discrete focal positions, with an image of the sample 30 being obtained at each of the discrete focal positions during the auto-focus sweep in the z-direction. In the examples provided above, the sweep may cover a focal distance or range of at least 300 µm or more.

Thereafter, at step 154, each of the images acquired from step 152 are analyzed to obtain a value based on one or more figures of merit (FOMs). Next, as indicated at step 156, a mathematical model defining a curve that best fits the FOM data points is determined. Subsequently, at step 158, the fitted curve is analyzed to identify a focal position that corresponds to the optimal focal position. For example, depending on the FOM selected, the optimal focal position may correspond to the maximum or minimum of the fitted curve. Finally, once the optimal focal position is determined, the process 150 continues to step 160, and the lens 28 of the sample arm 32 is controlled (e.g., by the lens control mechanism 60) to the selected focal position.

As will be understood, the various techniques described above and relating auto-ranging and auto-focusing in an optical coherence tomography imaging system are provided herein by way of example only. Accordingly, it should be understood that the present disclosure should not be construed as being limited to only the examples provided above. Further, it should be appreciated that the above-discussed techniques may be implemented in any suitable manner, including hardware (e.g., suitably configured circuitry), software (e.g., via a computer program including executable code stored on one or more tangible computer readable medium), or via using a combination of both hardware and software elements. Thus, the term "code," as used herein, may refer to machine-readable code (e.g., readable by a computer and/or processor) that may be stored in a machine-readable storage medium (e.g., disk, hard drive, optical drive, flash memory, etc.) for execution by a processor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An optical coherence tomography (OCT) imaging system comprising:
    a light source configured to emit light;
    a beam splitter configured to,
    receive the light from the light source,
    split the light into a first light portion directed along a sample arm comprising a sample and a second light portion directed along a reference arm comprising a reference mirror,
    receive a first reflected light portion from the sample arm and a second reflected light portion from the reference arm, and
    combine the first and second reflected light portions to obtain an interference signal; and
    a controller comprising logic configured to perform an auto-ranging process to match the reference arm with the sample arm, wherein matching the reference arm with the sample arm comprises;
    adjusting the reference arm to each of a plurality of discrete reference arm positions over a distance;
    acquiring a scan of the sample at each reference arm position;
    determining, for each scan, a figure of merit value; and
    selecting the reference arm position having a figure of merit value indicating a match with the reference arm.

2. The OCT imaging system of claim 1, comprising a reference arm adjustment control device, wherein the controller is configured to provide the selected reference arm position to the reference arm adjustment control device, and wherein the reference arm adjustment control device is configured to adjust the path length of the reference arm based on the selected reference arm position.

3. The OCT imaging system of claim 2, wherein the reference arm adjustment control device comprises a servomechanism.

4. The OCT imaging system of claim 2, wherein the reference arm adjustment control device comprises one or more rapid scanning optical delay (RSOD) lines.

5. The OCT imaging system of claim 1, wherein the figure of merit value comprises at least one of peak intensity, total integrated intensity, thesholded intensity, reflection characteristics, sharpness, entropy, and a moment about a mean.

6. The OCT imaging system of claim 1, wherein each reference arm position corresponds to an axial portion of the distance having boundaries, the portion defining a minimum axial scan depth.

7. The OCT imaging system of claim 6, wherein the boundaries of the axial portions of two adjacent reference arm positions partially overlap.

8. The OCT imaging system of claim 1, wherein the light source comprises a broadband light source comprising at least one of a super-luminescent diode (SLD), mode-locked laser, or an edge emitting light-emitting diode (LED), or some combination thereof.

9. The OCT imaging system of claim 1, comprising a spectral domain OCT imaging system, wherein the spectral domain OCT imaging comprises a spectrometer configured to analyze the interference signal in the spectral domain.

* * * * *